United States Patent [19]

Larkins, Jr.

[11] Patent Number: 4,918,241
[45] Date of Patent: Apr. 17, 1990

[54] METHOD OF PREPARING AROMATIC ETHERS FROM IODOAROMATIC COMPOUNDS

[75] Inventor: Thomas H. Larkins, Jr., Kingsport, Tenn.

[73] Assignee: Eastman Kodak Company, Rochester, N.Y.

[21] Appl. No.: 390,014

[22] Filed: Aug. 7, 1989

Related U.S. Application Data

[63] Continuation-in-part of Ser. No. 188,990, May 2, 1988, abandoned.

[51] Int. Cl.$^4$ .................... C07C 41/01; C07C 43/20
[52] U.S. Cl. .................... 568/648; 568/630
[58] Field of Search .................... 568/630, 648

[56] References Cited

U.S. PATENT DOCUMENTS

| | | | |
|---|---|---|---|
| 4,422,955 | 12/1983 | Bryant | 568/629 |
| 4,588,835 | 5/1986 | Torii et al. | 568/650 |
| 4,684,749 | 8/1987 | Paparatto | 568/797 |

Primary Examiner—Donald B. Moyer
Assistant Examiner—Karen Plue
Attorney, Agent, or Firm—Martin, Charles R.; William P. Heath, Jr.

[57] ABSTRACT

A method of preparing an ether corresponding to the structure

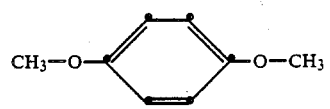

comprising reacting an aromatic iodine compound corresponding to the structure

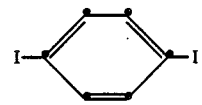

with methanol in the presence of a basic compound a copper catalyst and an amount of hydrogen which is effective to lower the oxidation state of the copper catalyst.

1 Claim, No Drawings

METHOD OF PREPARING AROMATIC ETHERS FROM IODOAROMATIC COMPOUNDS

This application is a continuation-in-part of Ser. No. 188,990, filed May 2, 1988 now abandoned.

This invention relates to a method of preparing aromatic ethers from iodoaromatic compounds and alcohols in the presence of a basic compound, a copper catalyst and hydrogen.

It has been discovered that the ether-forming reaction of an iodoaryl compound with an alcohol in the presence of a basic compound and a copper catalyst can be conducted with minimal formation of undesirable aryl by-products and high yield of desired products if the reaction occurs in the presence of a small but effective amount of hydrogen.

In summary, this invention can be thought of a method of preparing an ether corresponding to the structure

comprising reacting an aromatic iodine compound corresponding to the structure

with methanol in the presence of a basic compound, a copper catalyst and an amount of hydrogen which is effective to lower the oxidation state of the copper catalyst.

The use of an effective amount of hydrogen in the reaction allows the reaction to take place cheaply and efficiently, and as a result, this process is commercially practical.

The aromatic iodine compound is a well known compound prepared by well known processes. Other aromatic iodide compounds such as 2,6-diiodonaphthalene, can be used.

The copper catalyst can comprise any of the forms of copper useful in reactions of this type. Preferably, the catalyst is a compound containing plus one valence copper and more preferably the compound is an alkali metal salt of copper such as cuprous iodide.

The basic compound is preferably an alkali or alkaline earth metal hydroxide or a salt of a weak organic acid. Illustrative of suitable alkali or alkaline earth metal hydroxides are sodium, lithium, potassium and magnesium hydroxides. If the basic compound is a salt of a weak organic acid it is preferred that the organic acid be either carbonic acid or acetic acid. Suitable salts of this acids include sodium acetate, sodium carbonate and lithium acetate.

In this invention hydrogen is used as a reducing agent which is capable of lowering the oxidation state of the copper catalyst. Hydrogen in the form of hydrogen gas is most preferred. The amount of hydrogen is an amount effective to lower the oxidation state of the copper catalyst. The actual amount of hydrogen employed will vary depending on the reactants selected and reaction conditions.

In a preferred mode of conducting the invention the aromatic iodine compound, alcohol, base and copper catalyst are loaded into a rocking autoclave. The autoclave is closed and hydrogen gas is pumped in at room temperature. In a reaction mixture with about 10 grams of the iodoaromatic compound, one gram of copper catalyst, 7 grams of base, and about 100 mL of the alcohol, a charge of 100 psig of hydrogen gas is sufficient to minimize the production of undesirable aryl by-products.

Once the ether-forming ingredients and the hydrogen are present in the closed autoclave the autoclave is heated so that the reaction is conducted at a temperature of about 160° C. to about 225° C., and preferably at a temperature of from about 175° C. to about 205° C. The reaction is conducted at a pressure of about 1–200 atm, and preferably about 1–100 atm pressure. The autoclave initially heated gradually for up to one hour until the reaction temperature is achieved and the reaction temperature maintained for about 1–3 hours. After the reaction is completed the autoclave is cooled gradually for about one hour, after which the pressure can be vented and the autoclave opened in order to collect the final product. This reaction, using an effective amount of hydrogen, is characterized by a high yield of desired reaction product and a minimum amount of the undesirable aryl by-products which would otherwise result from various degradative pathways.

The hydroquinone dimethyl ether prepared in this process is a standard commercial chemical with known uses. For example on Pages 619 and 620 of the Eleventh Edition of Hawley's Condensed Chemical Dictionary, it is reported that hydroquinone dimethyl ether is useful as a weathering agent in paints and plastics. This compound is used as a weathering agent by adding the compound to the paints or plastics using known techniques.

EXAMPLE 1

The following experiment was conducted to demonstrate the ether-forming reaction in the absence of the reducing agent used in this invention. A 300 mL Hastelloy C rocking autoclave was loaded with 10.0 g p-diiodobenzene (0.030M), 1.0 cuprous iodide, 7.4 g (0.09M) anhydrous sodium acetate, and 100 mL methanol. The autoclave was closed and 100 psig nitrogen gas was added at room temperature. The autoclave was heated to 200° C. over a 45-minute period and held at 200° C. for two hours. The autoclave was cooled over a one-hour period. The pressure was vented and the autoclave was opened. As determined by gas chromatographic methods of analysis the liquid product contained 0.005M iodobenzene, 0.007M anisole, 0.005M benzene, 0.002M hydroquinone dimethyl ether, 0.009M p-iodoanisole, 0.001M p-diiodobenzene and trace amounts of several unidentified components. The formation of such large amounts of degradation products other than the hydroquinone dimethyl ether product is unacceptable for a commercial process.

EXAMPLE 2

Example 1 was repeated except that 100 psig hydrogen gas was used in place of 100 psig nitrogen gas. The liquid product contained 0.001M anisole, 0.001M iodobenzene, 0.004M hydroquinone dimethyl ether, 0.020M p-iodoanisole, and 0.004M p-diiodobenzene. This demonstrates the ability of the hydrogen gas to prevent degradation during the reaction and increase the amount of hydroquinone dimethyl ether.
I claim:
1. A method of preparing the ether
comprising reacting the compound
with methanol in the presence of a basic compound, a copper catalyst and an amount of hydrogen which is effective to lower the oxidation state of the copper catalyst.
* * * * *